US008236259B2

(12) United States Patent
Gracias et al.

(10) Patent No.: US 8,236,259 B2
(45) Date of Patent: Aug. 7, 2012

(54) SELF-ASSEMBLED, MICROPATTERNED, AND RADIO FREQUENCY (RF) SHIELDED BIOCONTAINERS

(75) Inventors: David H. Gracias, Baltimore, MD (US); Barjor Gimi, Irving, TX (US); Zaver M Bhujwalla, Baltimore, MD (US)

(73) Assignee: Johns Hopkins University, Baltimore, MD (US)

( * ) Notice: Subject to any disclaimer, the term of this patent is extended or adjusted under 35 U.S.C. 154(b) by 1263 days.

(21) Appl. No.: 11/491,829

(22) Filed: Jul. 24, 2006

(65) Prior Publication Data

US 2007/0020310 A1 Jan. 25, 2007

Related U.S. Application Data

(60) Provisional application No. 60/701,903, filed on Jul. 22, 2005.

(51) Int. Cl.
*B01L 3/00* (2006.01)
(52) U.S. Cl. ........ 422/547; 438/669; 977/700; 977/902; 977/904; 977/905; 977/906; 977/915
(58) Field of Classification Search .................. 422/102, 422/547; 438/669; 977/700, 902, 904, 905, 977/906, 915
See application file for complete search history.

(56) References Cited

U.S. PATENT DOCUMENTS

| | | | |
|---|---|---|---|
| 2,369,392 A | 2/1965 | Ringer | |
| 5,402,926 A | 4/1995 | Takeuchi et al. | |
| 5,688,486 A | 11/1997 | Watson et al. | |
| 6,432,253 B1 | 8/2002 | Chung | |
| 7,393,924 B2 * | 7/2008 | Vitaliano et al. | ............ 530/350 |
| 2004/0028694 A1 * | 2/2004 | Young et al. | ............ 424/190.1 |
| 2007/0141163 A1 * | 6/2007 | Vitaliano et al. | ............ 424/490 |
| 2009/0311190 A1 * | 12/2009 | Gracias et al. | ............ 424/9.3 |

OTHER PUBLICATIONS

Bartels, L.W., et al., "MR Imaging of Vascular Stents: Effects of Susceptibility, Flow, and Radiofrequency Eddy Currents", J Vasc Intery Radiol 2001; 12:365-371.
Bennett, L.H., et al., "Artifacts in Magnetic Resonance Imaging from Metals", Journal of Applied Physics, 79 (8), 1996, 4712-4714.
Green, P.W., et al., "Demonstration of Three-Dimensional Microstructure Self-Assembly", Journal of Microelectromechanical Systems, vol. 4, No. 4, Dec. 1995, 170-176.
Desai, T.A., et al., "Nanoporous Microsystems for Islet Cell Replacement", Advanced Drug Delivery Reviews, 56 (2004), 1661-1673.
Fireman, Z, et al., "Diagnosing Small Bowel Crohn's Disease with Wireless Capsule Endoscopy", Gut (2003) 52, 390-392.

(Continued)

*Primary Examiner* — Brian J Sines
(74) *Attorney, Agent, or Firm* — Ward and Smith, P.A.

(57) ABSTRACT

The present invention relates to a nanoscale or microscale container for encapsulation and delivery of materials or substances, including, but not limited to, cells, drugs, tissue, gels and polymers contained within the container, with subsequent release of the therapeutic materials in situ, methods of fabricating the container by folding a 2D precursor into the 3D container, and the use of the container in in-vivo or in-vitro applications. The container can be in any polyhedral shape and its surfaces can have either no perforations or nano/microscale perforations. The container is coated with a biocompatible metal, e.g. gold, or polymer, e.g. parylene, layer and the surfaces and hinges of the container are made of any metal or polymer combinations.

12 Claims, 5 Drawing Sheets

OTHER PUBLICATIONS

Gracias, D.H. et al., "Fabrication of Micrometer-Scale, Patterned Polyhedra by Self-Assembly", Advanced Materials (2002), 14, No. 3, Feb. 5, 2002, 235-238.

Harsh, K.F., et al., "Solder Self-Assembly for Three-Dimensional Microelectromechanical Systems", Sensors and Actuators (1999), 77, 237-244.

Hui, E.E., et als., "Single-Step Assembly of Complex 3-D Microstructures", IEEE 13th International Conference on Micro Electro Mechanical Systems (2000), 602-607.

Kost, J. and Langer, R., "Responsive Polymeric Delivery Systems", Advanced Drug Delivery Reviews 46 (2001), 125-148.

Lanza, R.P., et al., "Encapsulated Cell Technology", Nature Biotechnology, V. 14, Sep. 14, 1996, 1107-1111.

Leoni, L., et al., "Micromachined Biocapsules for Cell-Based Sensing and Delivery", Advanced Drug Delivery Reviews 56 (2004), 211-229.

Orive, G., et al., "Encapsulated Cell Technology: From Research to Market" Trends in Biotechnology, Sep. 20, 2002 (9): 382-7.

Santini, J.T., Richards, A., Scheidt, R., Cima, M.J. and Langer, R., "Microchips as Controlled Drug-Delivery Devices", Agnew. Chem. Int. Ed. (2000), 39, 2396-2407.

Santini, J.T., et al., "A Controlled-Release Microchip", Nature, V. 397, Jan. 28, 1999, 335-338.

Schueler, B.A., et al., "MRI Compatibility and Visibility Assessment of Implantable Medical Devices", Journal of Magnetic Resonance Imaging (1999), v9, 596-603.

Shenhav, A., et al., "Gradient Field Switching as a Source for Artifacts in MR imaging of Metallic Stents", Magnetic Resonance in Medice (2004), v. 52, 1465-1468.

Simpson, N.E., et al., "NMR Properties of Alginate Microbeads", Biomaterials (2003) 24, 4941-4948.

Smela, E., et al., "Controlled Folding of Micrometer-Size Structures" Science v. 268, Jun. 23, 1995, 1735-1738.

Syms, R.R.A., et al., "Surface Tension-Powered Self-Assembly of Microstructures—The State-of-the-Art", Journal of Microelectromechanical Systems, vol. 12, No. 4, Aug. 2003, 387-417.

Thomlinson, R.H., et al., "The Histological Structure of Some Human Lung Cancers and the Possible Implications for Radio-Therapy", The British Journal of Cancer, Dec. 9, 1955, 539-549.

Ziaie, B., et al., "Hard and Soft Micromachining for BioMEMS: Review of Techniques and Examples of Application in Microfluidics and Drug Delivery", Advanced Drug Delivery Reviews 56 (2004), 145-172.

Leong et al., "Surface Tension-Driven Self-Folding Polyhedra," Langmuir 23:8747-8751 (2007).

Filipiak et al., "Hierarchical Self-Assembly of Complex Polyhedral Microcontainers," J. Micromech. Microeng. 19 (2009).

Rodney S. Ruoff, et al., "Single Crystal Metals Encapsulated in Carbon Nanoparticles", Science, vol. 259, Jan. 15, 1993, pp. 346-348.

* cited by examiner

SELF-ASSEMBLED, MICROPATTERNED, AND RADIO FREQUENCY (RF) SHIELDED BIOCONTAINERS

CROSS-REFERENCE TO RELATED APPLICATIONS

This application claims priority to U.S. provisional application No. 60/701,903, filed Jul. 22, 2005, the entire contents of which is incorporated herein by reference.

GOVERNMENT RIGHTS

This research was supported in part by the National Institutes of Health (NIH P50 CA 103175). The government of the United States may have rights to this invention.

FIELD OF THE INVENTION

The present invention relates to a microfabricated nano or micro scale container for encapsulation and delivery of materials or substances including, but not limited to, biological media including cells, pharmaceutical agents, compositions, drugs, tissue, gels and polymers contained within the container, with subsequent release of the therapeutic materials in situ, methods of making the container and methods of using the container in in vivo or in vitro applications.

BACKGROUND OF THE INVENTION

In recent years, advances in regenerative medicine have inspired therapies targeted at the cellular level. These therapies seek to implant cells or cellular clusters, manipulate cellular pathways, and target the delivery of drugs. For example, a wide range of cell lines have been enclosed within semipermeable and biocompatible immobilization devices that control the bidirectional diffusion of molecules and cell release (R. P. Lanza, J. L. Hayes, W. L. Chick, Nat. Biotechnol. 14, 1107 (1996); G. Drive, R. M. Hernandez, A. R. Gascon, M. Igartua, J. L. Pedraz, J. L., Trends in Biotechnol. 20, 382 (2002); N. E. Simpson, S. C. Grant, S. J. Blackband, I. Constantinidis, Biomaterials 24, 4941 (2003)). Concurrent advances in microtechnology have revolutionized medicine, as new implantable devices, microarrays, biocapsules and microprobes are developed. These devices have facilitated cellular encapsulation, on-demand drug release, and early diagnosis of diseases (J. T. Santini, M. J. Cima, R. Langer, Nature 397, 335 (1999); J. Kost, R. Langer, Adv. Drug Delivery Rev. 6, 19 (1991); L. Leoni, T. A. Desai, Adv. Drug Delivery Rev. 56, 211 (2004); B. Ziaie, A. Baldi. M. Lei, Y. Gu, R. A. Siegel, Adv. Drug Delivery Rev. 56, 145 (2004); T. A. Desai, T. West, M. Cohen, T. Boiarski, A. Rampersaud, Adv. Drug Delivery Rev. 56, 1661 (2004); J. T. Santini, A. C. Richards, R. Scheidt, M. J. Cima, R. Langer, Angew. Chem. 39, 2396 (2000); Z. Fireman, E. Mahajna, E. Broide, M. Shapiro, L. Fich, A. Sternberg, Y. Kopelman, E. Scapa, Gut 52, 390 (2003)). In contrast to polymeric, hydrogel, and sol-gel based processes that have been used for encapsulation and delivery, conventional silicon (Si) based microfabrication has high reproducibility, provides mechanical and chemical stability, and allows the incorporation of electronic and optical modules within the device, thereby facilitating wireless telemetry, remote activation and communication, in vivo. However, Si based microfabrication is inherently a two dimensional (2D) process and it is extremely difficult to fabricate three-dimensional (3D) systems using conventional microfabrication (M. Madou, Fundamentals of Microfabrication (CRC, Boca Raton, Fla., 1997)). A 3D medical device has several advantages over its 2D counterpart: (a) a larger external surface area to volume ratio, thereby maximizing interactions with the surrounding medium, and providing space to mount different diagnostic or delivery modules, (b) a finite volume allowing encapsulation of cells and drugs, and (c) a geometry that reduces the chances of the device being undesirably lodged in the body.

In one aspect of the present invention, biocontainers have been fabricated by a strategy that combines the advantages of three-dimensionality with the desirable aspects of Si based microfabrication to facilitate the delivery of therapeutic agents in situ. For example, the containers are loaded with microbeads or cells embedded in a gel, and thus can be used either in conjunction with present day immobilization systems used in cell encapsulation technology, or they can be used independently. In another aspect, the biocontainers also can be used for encapsulation of functional cells within the porous containers for in vitro and in vivo release of therapeutic agents with, or without, immunosuppression. For example, the containers can be used for encapsulation and delivery of insulin secreting cells for implantation in patients with diabetes, for placing tumor innocula in animal models where constraining cells within a small region is necessary, and for delivery of functional neuronal PC12 cells. In some embodiments, the faces of the container are patterned with microscale perforations, allowing control over perfusion and release of its contents with the surrounding medium. In another aspect, the containers of the present invention are easily detected and non-invasively tracked using conventional magnetic resonance imaging (MRI) and do not require the presence of a contrast agent.

SUMMARY OF THE INVENTION

The present invention provides nanoscale or microscale containers for encapsulation and delivery of materials or substances, including, but not limited to, cells, drugs, tissue, gels and polymers contained within the container, with subsequent release of the therapeutic materials in situ, methods of fabricating the container by folding a 2D precursor into the 3D container, and the use of the container in in-vivo or in-vitro applications. In one embodiment of the present invention, a three-dimensional container comprises a multitude of two-dimensional faces that form a hollow, polyhedral shape and containing a fillable center chamber, wherein a size of the container is microscale or nanoscale. In another embodiment, the two-dimensional faces of the container are patterned with perforations or pores. In another embodiment, the perforations or pores are created photolithographically. In another embodiment, the perforations or pores have a size from about 0.1 nm to about 100 microns. In another embodiment, the container is fabricated from at least one material selected from the group consisting of a metal, a polymer, a glass, a semiconductor, an insulator, and combinations thereof. In another embodiment, the metal is copper or nickel. In another embodiment, the container is a Faraday cage. In another embodiment the container is coated with a biocompatible material. In another embodiment, the biocompatible material is a metal, a polymer, or a combination thereof. In another embodiment, the fillable center chamber of the container is filled with at least one substance comprising contents of the container. In another embodiment, perforations or pores in the two-dimensional faces of the container allow release of the contents of the container. In another embodiment, at least one substance is a therapeutic agent. In another embodiment, the therapeutic agent is selected from the group consisting of a cell, a pharmaceutical agent, a composition, a tissue, a gel, and a polymer. In another embodiment, the container is administered to a subject and location of the container in the subject is non-invasively tracked by magnetic resonance imaging. In another embodiment, the container is imaged with negative contrast relative to background or positive contrast relative to background.

The present invention also provides a method of fabricating a three-dimensional container comprising a multitude of two-dimensional faces that form a hollow polyhedral shape and containing a fillable center chamber, the method comprising the steps: (a) fabricating a multitude of two dimensional faces; (b) patterning the fabricated two-dimensional faces; (c) patterning at least one hinge on the patterned two dimensional face to form a hinged edge; (d) joining a hinged edge of a first patterned two dimensional face to a hinged edge of a second patterned two dimensional face to form a hinged joint; (e) repeating step (d) to form a two dimensional precursor template having hinged joints between adjacent two dimensional faces; (f) liquefying the hinges of the two-dimensional template using heat; and (g) self-assembling the three-dimensional container. In another embodiment, the hinges of step (c) of the method comprise a material that can be liquefied. In another embodiment, the material is a solder, a metallic alloy, a polymer or a glass. In another embodiment, step (a) of the method further comprises the steps (i) spinning a sacrificial film on a substrate to form a first layer; (ii) layering a conductive second layer on the first layer; and (iii) patterning the layered substrate by photolithography. In another embodiment, the container has a size that is microscale or nanoscale. In another embodiment, in step (b) of the method, the two-dimensional faces are patterned with perforations or pores. The perforations or pores are created photolithographically. In another embodiment, the perforations or pores have a size from about 0.1 nm to about 100 microns. In another embodiment, the container is a Faraday cage.

The present invention further provides a method of imaging a three-dimensional container comprising a multitude of two-dimensional faces that form a hollow polyhedral shape and containing a fillable center chamber that has been implanted into a subject, the method comprising the steps of: (i) loading the fillable center chamber of the container with at least one substance to form a loaded container; (ii) administering the loaded container to the subject; and (iii) noninvasively tracking the container of step (ii) in the subject by magnetic resonance imaging. In another embodiment, perforations or pores in the two-dimensional faces of the container allow release of the substance in the fillable center chamber. In another embodiment, the at least one substance of step (i) is a therapeutic agent. In another embodiment, the therapeutic agent is selected from the group consisting of a cell, a pharmaceutical agent, a composition, a tissue, a gel, and a polymer.

DETAILED DESCRIPTION OF THE INVENTION

Figure 1:
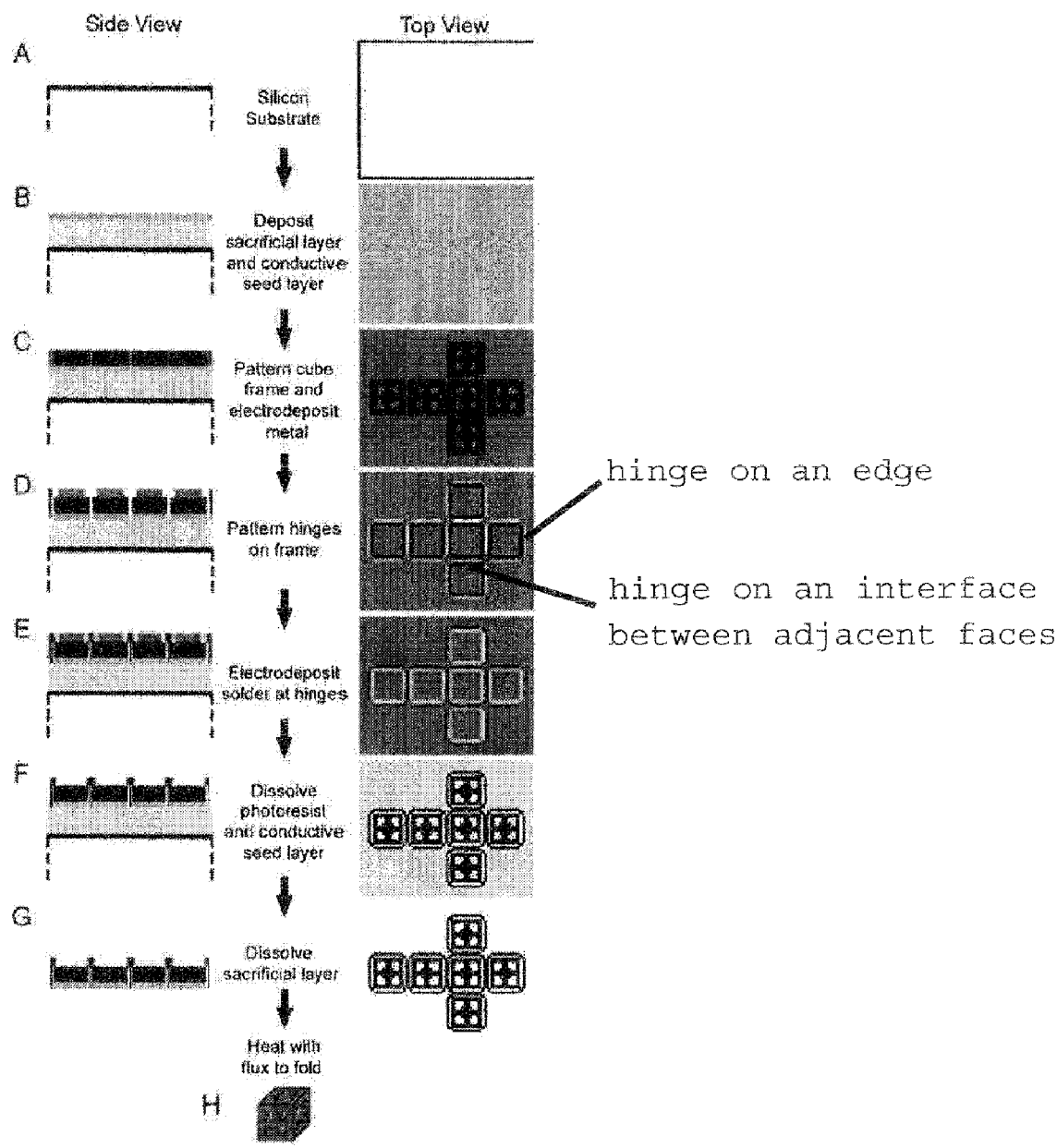
FIG. 1 is a schematic diagram of the process flow used to fabricate the 3D containers of the present invention.

The term "colloid" or "colloidal" as used herein refers to a substance made up of a system of particles dispersed in a continuous medium.

Materials can react quite differently in the presence of an external magnetic field. Their reaction is dependent on a number of factors, including, but not limited to, the material's molecular structure, its atomic structure, and the net magnetic field associated with the atoms. Most materials can be classified as ferromagnetic, diamagnetic, or paramagnetic.

The term "diamagnetic" as used herein refers to materials having a very weak form of magnetism exhibited only in the presence of an external magnetic field, which is the result of changes in the orbital motion of electrons due to the external magnetic field. The induced magnetic moment in a diamagnetic material is very small and in a direction opposite to that of the applied field. Examples of diamagnetic materials include, but are not limited to, copper, silver and gold.

The term "ferromagnetic" refers to materials having large and positive susceptibility to an external magnetic field. Ferromagnetic materials have some unpaired electrons so their atoms have a net magnetic moment. They exhibit a strong attraction to magnetic fields and are able to retain their magnetic properties after the external field has been removed. Examples of ferromagnetic materials include, but are not limited to, iron, nickel and cobalt.

The term "paramagnetic" refers to materials having a small and positive susceptibility to magnetic fields, which are slightly attracted by a magnetic field. Paramagnetic materials do not retain magnetic properties when the external field is removed. These paramagnetic properties are due to the presence of some unpaired electrons and the realignment of the electron orbits caused by the external magnetic field. Examples of paramagnetic materials include, but are not limited to, magnesium, molybdenum, and lithium.

The term "Faraday cage" as used herein refers to an enclosure designed to block the effects of an electric field, while allowing free passage to magnetic fields. (See E. M. Purcell, Electricity and Magnetism, Berkeley Physics Course Volume 2 (McGraw Hill, Ma., 1985)). Such an enclosure also is called a Faraday shield, Faraday shielding, Faraday screen, Faraday electrostatic shield, or shielded room.

The term "gel" as used herein refers to an apparently solid, jellylike material formed from a colloidal solution. By weight, gels are mostly liquid, yet they behave like solids. The term "solution" refers to a homogeneous mixture of one or more substances (the solutes) dissolved in another substance (the solvent).

The term "magnetic field" as used herein refers to the region in space surrounding a magnetic body or entity, such as a permanent magnet or a conductor carrying a current, where an appreciable magnetic force is present. Such a field is represented by magnetic lines of force. In an electromagnetic field, for example, the magnetic field is perpendicular to the electrical field.

The term "magnetic field strength" or "magnetic field intensity" ("H") refers to the intensity of a magnetic field at a given point. Magnetic field strength is a vector quantity usually expressed in amperes per meter or in oersteds.

The term "magnetic resonance imaging: or "MRI", refers to a noninvasive imaging technique that uses the interaction between radio frequency pulses, a strong magnetic field, and an subject to construct images in slices/planes from the nuclear magnetic resonance (NMR) signal obtained from the hydrogen atoms inside the subject. The principle behind all MRI is the resonance equation, $$\nu = \gamma B_0 \quad \text{(Equation 1)}$$

which shows that the resonance frequency $\nu$ of a spin is proportional to the magnetic field $B_0$, it is experiencing, where $\gamma$ is the gyromagnetic ratio.

As used herein, the term "microscale" refers to particles that measure from about 1 μm or $1 \times 10^{-6}$ meters to about 999 μm in at least one dimension. As used herein the term "nanoscale" refers to particles that measure from about 1 nanometer or $1 \times 10^{-9}$ meters to about 999 nanometers.

The term "magnetic field gradient" refers to a variation in the magnetic field with respect to position. A one-dimensional magnetic field gradient is a variation with respect to one direction, while a two-dimensional gradient is a variation with respect to two directions. The most useful type of gradient in magnetic resonance imaging is a one-dimensional linear magnetic field gradient. A one-dimensional magnetic field gradient along the x axis in a magnetic field, $B_o$, indicates that the magnetic field is increasing in the x direction. The symbols for a magnetic field gradient in the x, y, and z directions are $G_x$, $G_y$, and $G_z$.

In physics, the term "magnetic moment" or "dipole moment" refers to the pole strength of a magnetic source multiplied by the distance between the poles ($\mu = pd$), and is a measure of the strength of the magnetic source. The magnetic moment in a magnetic field is a measure of the magnetic flux set up by gyration of an electron charge in a magnetic field.

The term "micropattern" or "micropatterned" as used herein refers to any arbitrary two-dimensional pattern having microscale features. The term "nanopattern" or "nanopatterned" as used herein refers to any arbitrary two-dimensional pattern having microscale features. According to the present invention, the containers are patterned with perforations or pores ranging in size from about 0.1 nm to about 100 microns.

The term "oscillating magnetic field" or "oscillatory magnetic field" refers to a magnetic field that periodically increases and decreases its intensity, m, or which otherwise varies over time.

The containers of the present invention may be in any polyhedral shape. The term "polyhedral" as used herein refers to of or relating to or resembling a polyhedron. The term "polyhedron" refers to a three dimensional object bounded by plane polygons or faces. The term "polygon" refers to a multisided geometric figure that is bound by many straight lines, such as a triangle, a square, a pentagon, a hexagon, a heptagon, an octagon, and the like. For example, the containers of the present invention may be a cube or a tetrahedral.

The term "radiofrequency" as used herein refers to a frequency or interval of frequencies within the electromagnetic spectrum used for communications, usually defined as spanning from about 3 kHz to about 300 GHz, which corresponds to wavelengths of about 100 km to about 1 mm respectively.

The term "resistance" refers to a measure of the degree to which an object opposes the passage of an electric current as represented by the equation, $R = V/I$, where R is the resistance of the object (usually measured in ohms, equivalent to $J\,s/C^2$); V is the potential difference across the object, usually measured in volts, and I is the current passing through the object, usually measured in amperes).

The presence of any substance in a magnetic field alters that field to some extent. The term "susceptibility effect" refers to the degree to which a substance's inherent magnetic moment produces polarization when placed in a magnetic field.

The terms "two-dimensional" or "2D" are used interchangeably herein to refer to a figure, object or area that has height and width, but no depth, and is therefore flat or planar.

The terms "three-dimensional" or "3D" are used interchangeably herein to refer to a figure, object or area that has height, width, and depth.

The containers of the present invention are fabricated using at least one material selected from the group consisting of a metal (meaning an element that is solid, has a metallic luster, is malleable and ductile, and conducts both heat and electricity), a polymer, a glass (meaning a brittle transparent solid with irregular atomic structure), a semiconductor (meaning an element, such as silicon, that is intermediate in electrical conductivity between conductors and insulators, through which conduction takes place by means of holes and electrons), and an insulator (meaning a material that is a poor conductor of heat energy and electricity). They were designed as miniature Faraday cages in order to facilitate detection in MRI. The containers shield (meaning protect, screen, block, absorb, avoid, or otherwise prevent the effects of) the oscillating magnetic fields in MM that arise from radio frequency (RF) pulses and magnetic field gradients in an imaging sequence. This shielding occurs as a result of eddy currents (meaning circulating currents induced in a conductor moved through a magnetic field, or which is subjected to a varying magnetic field) generated in the frame of the container that induce a local magnetic field, which interferes destructively with the external magnetic field.

In one aspect, the present invention describes the self-assembly of 3D metallic containers from 2D photolithographically micropatterned precursors. The terms "photolithography", "photo-lithography", or "photolithographic process" refer to a lithographic technique in which precise patterns are created on substrates, such as metals or resins, through the use of photographically-produced masks. Typically, a substrate is coated with a photoresist film, which is dried or hardened, and then exposed through irradiation by light, such as ultraviolet light, shining through the photomask. The unprotected areas then are removed, usually through etching, which leaves the desired patterns.

The containers of the present invention are self-folding and self-assembling. The at least one hinge of these structures comprises a material, including but not limited to, a solder (meaning an alloy formulated to have a specific melting point for use in joining metals), a metallic alloy (meaning a mixture containing two or more metallic elements or metallic and nonmetallic elements usually fused together or dissolving into each other when molten), a polymer or a glass that can be liquefied. The surface tension of the liquid hinge provides the force necessary to fold the 2D template into the 3D containers.

In another aspect, after self-assembly, the fillable center chamber of the containers of the present invention is available as a vessel for encapsulation of therapeutic agents. As used herein, the term 'therapeutic agent" refers to any pharmaceutical agent, composition, gene, protein, cell, molecule, or substance that can be used to treat, control or prevent a disease, medical condition or disorder. The term "composition" refers to a mixture of ingredients. The term "pharmaceutical composition," as used herein, refers to a composition, which has under gone federal regulatory review. The term "treat" or "treating" includes abrogating, substantially inhibiting, slowing or reversing the progression of a condition, substantially ameliorating clinical or symptoms of a condition, and substantially preventing the appearance of clinical or symptoms of a condition. The amount of a therapeutic agent that result in a therapeutic or beneficial effect following its administration to a subject, including humans, is a "therapeutic amount" or "pharmaceutically effective amount". The therapeutic or beneficial effect can be curing, minimizing, preventing or ameliorating a disease or disorder, or may have any other therapeutic or pharmaceutical beneficial effect. The term "disease" or "disorder," as used herein, refers to an impairment of health or a condition of abnormal functioning. The term "syndrome," as used herein, refers to a pattern of symptoms indicative of some disease or condition. The term "injury," as used herein, refers to damage or harm to a structure or function of the body caused by an outside agent or force, which may be physical or chemical. The term "condition," as used herein, refers to a variety of health states and is meant to include disorders, diseases, or injuries caused by any underlying mechanism or disorder, and includes the promotion of healthy tissues and organs.

In some embodiments, the fillable center chamber of the containers can be used to encapsulate such therapeutic agents as pharmaceutical agents or drugs, living tissue, gels and polymers, which subsequently are released in situ. As used herein, the term "polymer" refers to a natural or synthetic compound consisting of long, repeated and sometimes branched chains, built up from small subunits called monomers. Natural polymers include proteins (polymer of amino acids) & cellulose (polymer of sugar molecules). There are many examples of synthetic polymers.

In some embodiments, functional cells (e.g., pancreatic islet cells, neuronal PC12 cells) can be encapsulated for in vitro and in vivo release with or without immunosuppression. Such containers can be administered to a subject in need thereof by microinjection, either as a single biocontainer or as a group of biocontainers and are useful for imaging, diagnostics, and therapeutics.

For example, in one embodiment, the fillable center chambers of a multitude of containers were filled with cells that were embedded in a gel. These cells could be released by immersing the biocontainer in an appropriate solvent. The magnetic resonance (MR) images of the containers embedded in fluidic media suggest RF shielding and a susceptibility effect, providing characteristic hypointensity (darkness) within the container, thereby allowing the containers to be easily detected. This demonstration is the first step toward the design of 3D, micropatterned, non-invasively trackable, encapsulation and delivery devices.

In another aspect, cells within or proximal to implanted containers of the present invention can be imaged by MRI to evaluate the efficacy of the implant and the condition of the encapsulated cells.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limit of these smaller ranges, which may independently be included in the smaller ranges, is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and described the methods and/or materials in connection with which the publications are cited.

It must be noted that as used herein and in the appended claims, the singular forms "a", "and", and "the" include plural references unless the context clearly dictates otherwise. All technical and scientific terms used herein have the same meaning.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

EXAMPLES

The following examples are put forth to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Fabrication of the Containers

FIG. 1 is a schematic diagram of the process flow used to fabricate the 3D containers of the present invention.

First, a 5 µm thick sacrificial layer of polymethyl methacrylate (PMMA, MW=996 K) was spun on a silicon substrate. The term "spinning" as used herein refers to a process whereby a fluid is dropped on a rotating substrate. A 15 nm layer of chromium (Cr) and a 100 nm thick layer of copper (Cu) were evaporated on top of the PMMA coated wafer. The Cr layer functions as an adhesive promoter while the Cu layer functions as a conductive seed layer for subsequent electrodeposition. Since it is necessary to etch the Cr and Cu later in the process, it is necessary to minimize their thickness to achieve a rapid etch. However, to minimize the electrical resistance of the film across the wafer during electrodeposition, the material thickness has to be increased. A thickness of 125 nm was deemed optimal for the present application. After thin film deposition, the substrate was patterned using photolithography. The photoresist Shipley SPR220 (Rohm and Haas, www.rohmhaas.com) was first spun on the wafer substrate, the thickness of the photoresist was controlled by changing the spin speed and the number of coats. After a soft bake, the resist was exposed to UV light using a mask aligner. The photomask used to pattern the resist was a transparency mask with six 200 nm squares spaced 20 pm apart. After exposure, the wafer was developed and the thickness of the resist was measured using an Alpha-Step profilometer. Then, electrodeposition was used to build pattern the metallic faces of the container in the photoresist mold up to a height of 7-15 p.m, using commercial electrolytic solutions (Technic, Inc, www.technic.com) containing the metal ions of choice. Cu was electrodeposited followed by a thin layer (about 1 pm) of gold (Au) to form non-magnetic containers and a thin layer (about 1 pm) of nickel (Ni) to fabricate magnetic containers. The Au was used to protect the Cu surface from subsequent etching steps and render it inert.

A second round of photolithography was performed in order to pattern the hinges. A second layer of SPR200 was spun on the substrate and a hinge photomask was used to pattern the hinges. The hinge mask consisted of two kinds of hinges ($50 \times 160$ ($\mu m^2$ and $25 \times 160$ $\mu m^2$). The wider hinges were at the interfaces of adjacent faces while the narrower hinges were at the edges of the faces. Alignment marks were used to ensure perfect alignment of the hinges to the faces of the 2D precursor. Prior to hinge electrodeposition, the exposed Cu and Cr in the area of the hinges were etched using commercial etchants (APS-100 for Cu and CRE-473 for Cr, Technic, Inc, www.technic.com). Although the etchants have a high selectivity of Cu or Cr with respect to Ni or Au, the etch time was optimized to minimize damage to the Ni or Cu/Au frame of the container. Pure tin (m.p. 232° C.) or tin/lead (Sn/Pb: m.p. 183° C.) solder was then electroplated in the hinge regions. The height of the hinges was approximately 5 μm to about 15 μm depending on the face pattern and the type of metal used (wetting or non-wetting). After electrodeposition, the original seed layer was etched and the 2D precursor template was immersed in a solution of N-Methyl Pyrrolidone (NMP, which dissolves the sacrificial PMMA layer) to release the precursors from the wafer. Approximately 50 precursors then were scattered in a small crystallizing dish using a pipette. A very thin layer of RMA-2 flux, (Indium Corporation, www.indium.com, used to dissolve any oxide formed on the solder) was poured into the dish. The dish was then heated to 100° C. for about 2 min to about 3 min and then ramped up to about 250° C. to about-300° C. for 20 seconds. Because of the low volume of flux, the agitation was sufficient to correct for defects in the folding but not large enough to cause the crosses to collide into each other and become fused. The molten solder generated the force needed to fold the 2D precursors into 3D containers. On cooling, the containers were permanently held together by solid solder hinges.

Diamagnetic copper (Cu) containers were fabricated with linear dimensions of about 200 pm (where one picometer is $10^{-12}$ meter). As compared to smaller or larger sized biocapsules, the 200 pm size provides the maximum encapsulation volume while still allowing the diffusion of oxygen and nutrients to the cells. It is known that if cells are more than about 150 μm to about 200 μm away from the nearest blood vessel, the environment becomes hypoxic (R. H. Thomlinson and L. H. Gray, Brit. J. Cancer December 9, 539 (1955)). In principle, the fabrication strategy described herein also would work on smaller or larger size scales in the design of containers for other applications. The linear dimension of the container was orders of magnitude smaller than the wavelength of the oscillating magnetic field at 500 MHz, which is the highest operating frequency in our magnetic resonance (MR) scanners. Hence, the size of the perforations on the faces of the container had no detrimental effect on the shielding characteristics of the container. The thickness of the faces of the container was designed to be larger than the conductor skin depth at the frequency of the radiation. The term "skin depth" refers to a measure of the average depth of penetration of an electromagnetic field into a material. It is defined as the depth at which the primary electromagnetic (EM) field is attenuated by/decreases to (1/e) of the field at the surface, or to approximately 37% of its value at the surface of the shield (A. Tsaliovich, *Electromagnetic Shielding Handbook for Wired and Wireless Applications* (Kluwer Academic Publishers, MA, 1999)). A thicker container also has lower conductor resistance, ensuring that the eddy currents persist long enough to maintain shielding during the time of image acquisition. The skin depth of Cu at 500MHz is about 2.9 pm (C. Kittel, *Introduction to Solid State Physics*, (Wiley, N.Y., ed., at 7 (1995)); hence, containers were designed to have frames with thickness ranging from about 7 pm to about 15 pm.

Ferromagnetic nickel (Ni) containers in addition to the diamagnetic Cu containers described above were fabricated to investigate the effect of magnetic susceptibility on the MR images of the container. Magnetic field distortions including, but not limited to, shape, amplitude and phase distortions, resulting from the differences in magnetic susceptibility between an object and its surrounding medium cause a loss of phase coherence in the magnetization of the sample. Since the magnetic susceptibility of Cu is comparable to that of water, while that of Ni is orders of magnitude higher than that of water, a more pronounced distortion was expected for Ni containers in aqueous media (L. W. Bartels, et al., *J. Vasc. Interv. Radiol.* 12: 365 (2001)).

The strategy used to fabricate both the Cu and Ni containers involved the auto-folding of 2D metallic precursors using capillary forces. "Capillary action", "capillarity" or capillary motion, which are used interchangeably herein to refer to the ability of a narrow tube to draw a liquid upwards against the force of gravity, occurs when the adhesive intermolecular forces between the liquid and a solid are stronger than the cohesive intermolecular forces within the liquid. The same effect is what causes porous materials to soak up liquids. Previous demonstrations of auto-folding include the actuation of micrometer size components and the assembly of 3D complex structures (E. Smela, et al, *Science* 268: 1735 (1995); P. W. Breen et al., *J. Microelectromech. Syst.* 4: 170 (1995); K. F. Harsh et al., *Sens. Actuators A* 3: 237 (1999); E. E. Hui et al., *IEEEE 13th Int. Conf. On Micro Electro Mechanical Systems,* 602 (2000); D. H. Gracias, et al., *Adv. Mater.* 14: 235 (2002)).

According to one aspect of the present invention, 3D, hollow, perforated containers were fabricated from 2D precursors. The process used to fabricate the 2D precursors, which is an extension of the process described in Example 1, and required several additive layers, two photolithography steps, two electrodeposition steps, and a precise sequence of subtractive processes. Briefly, the process involved patterning the metallic 2D faces using photolithography and electrodeposition on top of a sacrificial layer. The versatility of the strategy was demonstrated by fabricating precursors whose faces contained two different patterns—one pattern comprised a square frame with open faces, while the other consisted of a microscale cross shaped pattern in the center of each face. In a second layer of photoresist, hinges were patterned on the edges of the frames. The width of the hinge between two adjacent faces was twice the width of the hinge at the edges so that all hinged joints had equal solder volume upon folding; the solder volume was critical to ensure a folding angle of 90° (R. R. A. Syms, et al., *J. Microelectromech. Syst.* 12: 387 (2003)). After the hinges were patterned, the 2D precursors were lifted off the wafer by dissolution of the sacrificial layer. The containers were self-assembled by heating the precursors above the melting point of the solder, wherein the liquid solder with high surface tension generated the force required to fold adjacent faces of the precursor.

Figure 2:
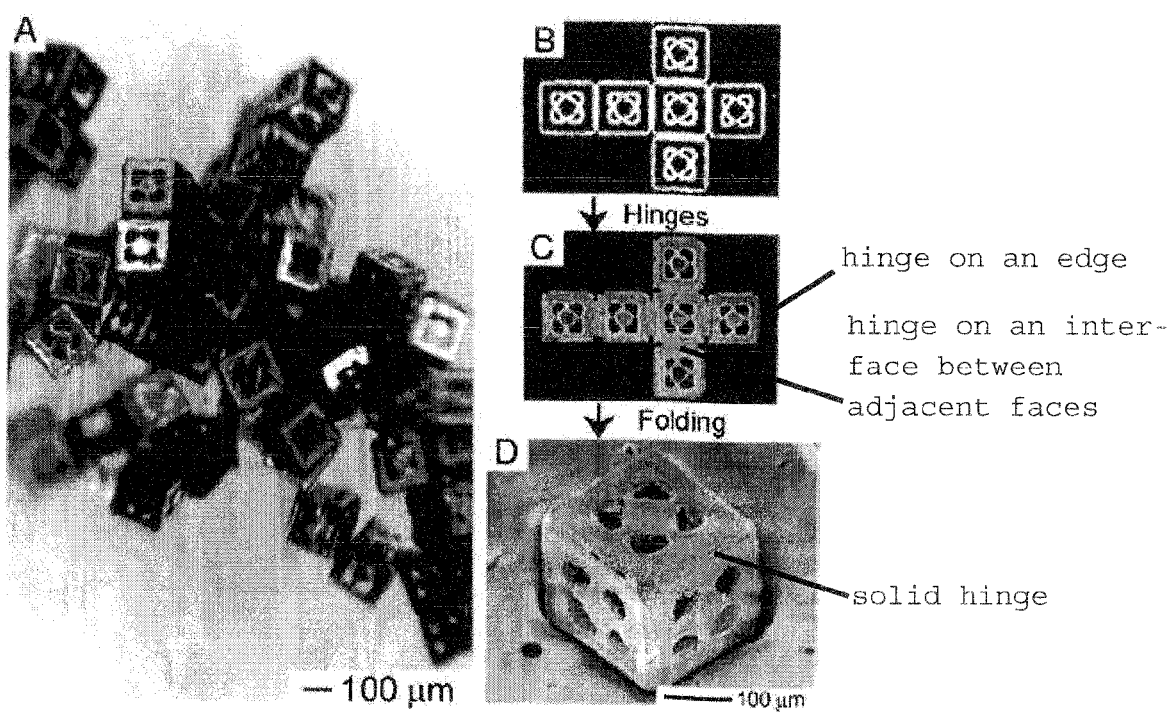
FIG. 2.(A) Optical image showing a collection of containers. (B-D) Optical and Scanning electron microscopy (SEM) images of micropatterned containers at different stages of the fabrication process; (B) the 2D precursor with electrodeposited faces, (C) the precursor with faces and hinges, and (D) the folded container.

FIG. 2A shows an optical image of a collection of containers that were fabricated using the process outlined above. The fabrication strategy allows a large number of containers to be constructed in a single process run. The primary yield-limiting factor was the error in estimating the volume of the solder to be electrodeposited at each hinge. The spacing between the adjacent faces was also critical—when the gap between faces was either too large or when the faces were fused, the yield of folding was greatly limited. FIGS. 2B-2D show optical and SEM images of the micropatterned containers at different stages of the fabrication process: the 2D precursor with electrodeposited faces, the precursor with faces and hinges, and the folded container.

Although an open-faced container is not ideal for an encapsulation device, since it is considerably leaky, open-faced containers were filled for easy visualization of their contents. For in vivo applications it may be desirable to use the described strategy to construct containers with selectively sealed or micro/nano perforated faces, and fabricate more complex, polyhedral containers with rounded vertices. An open-faced container (FIG. 3A) was loaded with microbeads since many cellular delivery techniques use microbeads with cells adhered to their surface. In order to load the container with microbeads, a suspension of the beads in ethanol was pipetted onto the container. The suspension entered the container as a result of capillary forces. When the ethanol evaporated, the beads were held together by weak van der Waals forces (meaning the weak intermolecular forces that arise from the transient polarization of a given molecule into a dipole) (FIG. 3B); the glass beads could be released by agitation of the container.

Figure 3:
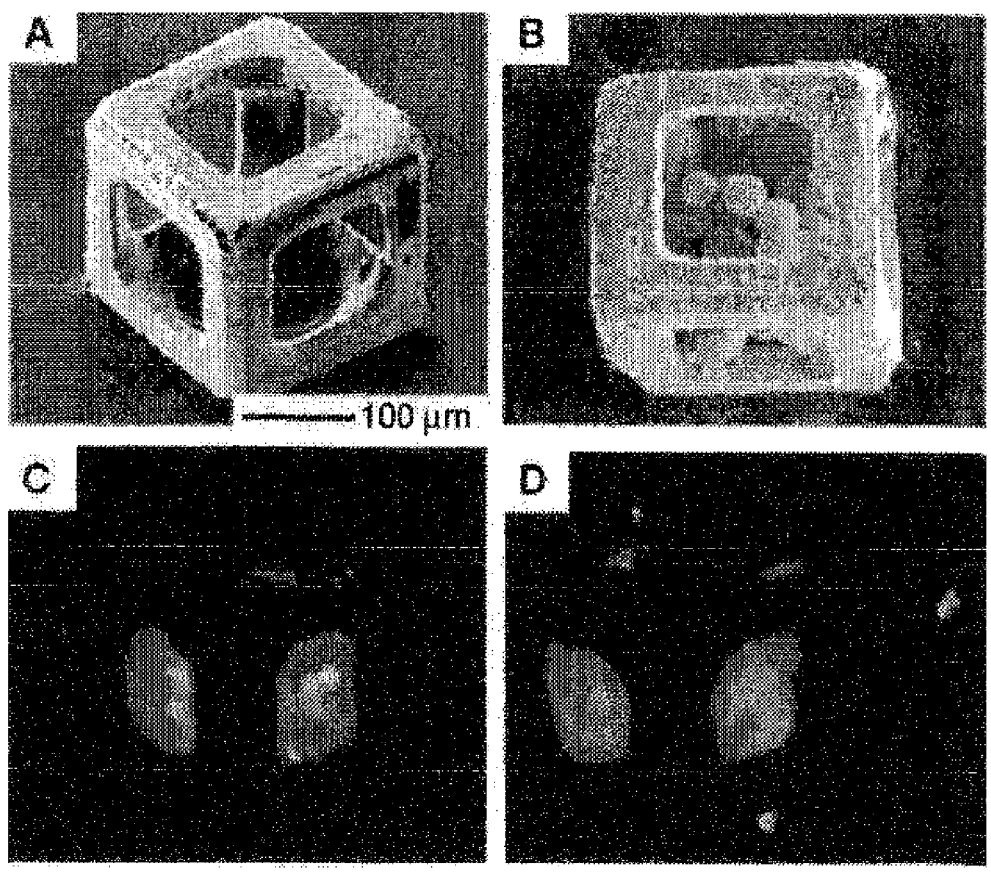
FIG. 3.(A) SEM image of a hollow, open-faced container. (B) SEM image of a container loaded with glass microbeads. (C) Optical image of a biocontainer loaded with MDAMB-231 breast cancer cells embedded than extra-cellular matrix (ECM) gel. (D) Release of the cells by immersion of the container in warm cell culture medium. (E) Optical image of a container loaded with a cell-ECM-agarose suspension stained with the fluorescent cell viability stain, Calcein-AM. (F) Release of the viable cells from the container on immersion in warm cell culture medium.

In order to demonstrate cellular encapsulation, MDA-MB-231 breast cancer cells in an extracellular matrix (ECM) suspension at 4° C., were loaded in the containers (FIG. 3C). As used herein, the term extracellular matrix refers to the complex structural entity surrounding and supporting cells that are found within mammalian tissues, as well as one or more of its constituents including, but not limited to, collagen, elastin, fibronectin and laminin. MDA-MB-231 cells are representative of rapidly proliferating cells and immortalized cells, such as βTC3 cells, used in diabetes therapy, and stem cells used in regeneration. On incubation at 37° C. for 5 min, the ECM suspension gelled; the cells were retained in the biocontainer and could be released by immersing the container in warm cell culture medium (FIG. 3D). It was also possible to load the biocontainers with a cell-ECM suspension within an agarose cavity. In this case, a suspension of 5% agarose gel was first micropipetted (60 μm tip) into the container using a stereotactic manipulator. The gel adhered to the sides of the container thereby sealing the faces and leaving a void in the center of the container. The cell-ECM suspension was then microinjected into this void, which was then sealed with a microdrop of agarose gel.

To demonstrate that the cells were viable in the biocontainer and on release, the cells were stained with the fluorescent dye, Calcein-AM (Sigma-Aldrich), which stains positively for live cells. FIG. 3E shows calcein-stained cells within the biocontainer and FIG. 3F shows release of live cells from the container on immersion in warm cell culture medium. The frames of the biocontainers used in this demonstration had a thin gold or platinum coating on the interior faces for biocompatibility, since gold and platinum are inert or unreactive materials. Pure tin and tin/lead based solders were used to fold the containers. It may be necessary to use other solders containing inert metals such as silver and gold for enhanced biocompatibility. It is also possible to increase the biocompatibility of the containers, by coating the entire folded container with a layer of an inert metal (by electrodeposition) or with polymers (by immersion or vapor coating).

Figure 4:
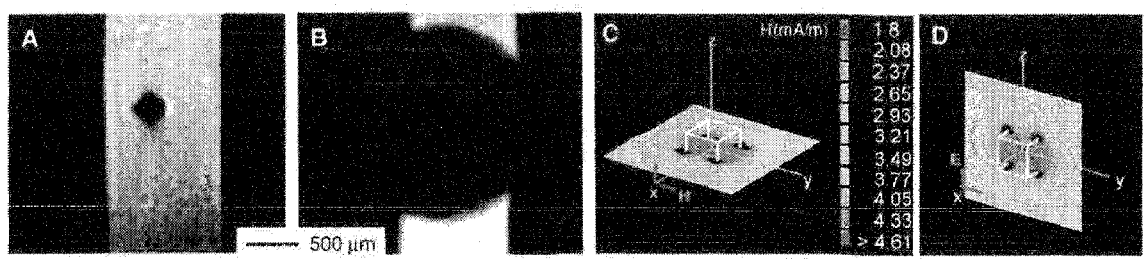
FIG. 4. MRI images of an open faced (A) non-magnetic Cu container and (B) ferromagnetic Ni container. (C-D) Finite element simulation results of the near magnetic field in the region of a Cu container, in the (C) xy and (D) yz central planes. The excitation comprised a linear polarized 500 MHz plane wave of 1 V/m, with the E and H fields in the z and y direction respectively. The magnetic field distortions and the shielding effect caused by the wire frame are evident.

Non-invasive detection of the containers was demonstrated by embedding the containers in 5% agarose gel and imaging them with MRI in a 500 MHz vertical bore Bruker Avance microimaging system. For the images shown here, a 3D FLASH sequence with the echo time (TE) in the range of 4-6 ms, a repetition time (TR) of 50 ms, flip-angle of 30°, and a spatial resolution of 25 μm×25 μm×20 μm was used. The containers also were imaged using a standard spin echo sequence (meaning a pulse sequence used in magnetic resonance imaging based on the detection of a spin or Hahn echo, which uses 90° radiofrequency pulses to excite the magnetism and one or more 180° pulses to refocus the spins to generate signal echoes named "spin echoes), with similar results. FIG. 4 shows MR images of a 900 μm diameter capillary containing a Cu (FIG. 4A) and a Ni (FIG. 4B) container embedded in agarose gel. A characteristic signature was observed for both the Cu and the Ni containers—there is a pronounced darkness in the region of each container. These hypointense (dark) signatures have been observed before in MRI of larger centimeter scale metallic coils (A. Shenhav, H. Azhari, *Magn. Reson. Med.* 52: 1465 (2004)). While the region of hypointensity (darkness) in the MR image was comparable to the size of the non-magnetic Cu container, it was much larger for the ferromagnetic Ni container due to a pronounced susceptibility effect (L. H. Bennett, et al., *J. Appl. Phys.* 79: 4712 (1996); B. A. Schueler, et al., *J. Magn. Reson. Imaging* 9: 596 (1999)). The images of containers made of a given material were similar for both open faced containers as well as cross faced containers, showing that the pattern of the faces had little bearing on the MR signature at this size scale.

RF shielding was simulated in a non-magnetic container with a finite element model for a 200 gm scale wire frame that was excited by a linear polarized electromagnetic wave. FIGS. 4C-4D are simulation results showing magnetic field distortions in the vicinity of the container and reduced field magnitude in the interior of the container.

Figure 5:
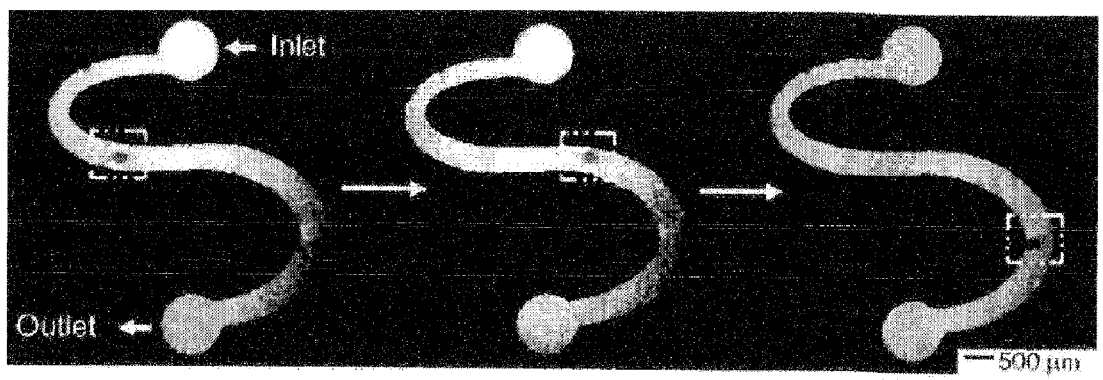
FIG. 5. MR tracking of a container in a fluidic channel. MR images of the container at different time points taken under pressure driven flow of the fluid.

For many biomedical applications it is necessary to non-invasively track an encapsulation device. The Cu container of the present invention could be tracked spatially and temporally with MRI in flow through an S-shaped 500 pm diameter fluidic channel. The channel was fabricated by molding poly dimethyl siloxane (PDMS) in an SU-8 photoresist mold that was patterned using photolithography. The channel was sealed with a second, flat, oxygen plasma treated PDMS layer. Polyethylene tubes were connected to the inlet and outlet ports of the channel, the channel was flushed with silicone oil, and the container was introduced into the channel. Under pressure driven flow, the container moved within the channel and was imaged at different positions; the sequence of MRI images is shown in FIG. 5. This ready trackability with MRI at very short echo times, without the need for a contrast agent, highlights a major advantage of the 3D metallic biocontainers of the present invention as compared to many other encapsulation systems.

Example 2

Simulation of Near Magnetic Fields in the Region of the Container

To demonstrate an RF shielding effect, the near magnetic field response in the vicinity of the container was simulated using a finite element electromagnetic simulation package, FEKO (EM Software & Systems-SA Ltd., www.feko.Info/). A full-wave method of moments approach was used to simulate the near magnetic field in the region of a 200 μm wire frame with wire segments of 8 μm radius, assuming perfect electric conductors coated with copper (conductivity=$5.813 \times 10^7$ S.m$^{-1}$). The simulation of the cubical wire frame model was performed with a linear polarized plane wave excitation at 500 MHz; we used an excitation source of 1 V/m incident on the wire frame, with E in the z direction and H in the y direction (FIG. 4C). The copper wire frame was assigned a relative permeability of 1, thereby simulating only the RF shielding effect and not the susceptibility effects. FIG. 4C shows the near magnetic field response in both the x-y and the y-z central planes.

In conclusion, the described strategy can be used to fabricate 3D, arbitrarily micropatternable, non-invasively trackable biocontainers that allow perfusion between the contents of the biocontainers and the surrounding medium. These biocontainers are encapsulation devices that do not lose their detectability when loaded with biological content. Due to their strength and high porosity, such metallic biocontainers are useful as basic elements of a scaffold to guide the growth of cells in 3D. Since the fabrication strategy described here is compatible with conventional 2D microfabrication, it also may be possible to add electromechanical modules for remote activation, wireless communication, signal processing, and biosensing to the faces of the biocontainers, to enable medical diagnostics and therapeutics. The present invention also envisions that such 3D containers, which function as small Faraday cages, will find utility in other applications requiring electromagnetic shielding in small volumes.

While the present invention has been described with reference to the specific embodiments thereof it should be understood by those skilled in the art that various changes may be made and equivalents may be substituted without departing from the true spirit and scope of the invention. In addition, many modifications may be made to adopt a particular situation, material, composition of matter, process, process step or steps, to the objective spirit and scope of the present invention. All such modifications are intended to be within the scope of the claims appended hereto.

What is claimed is:

1. A method of fabricating a three-dimensional container comprising a multitude of two-dimensional faces that form a hollow polyhedral shape and containing a fillable center chamber, wherein the multitude of two-dimensional faces are permanently held together by solid hinges, the method comprising:
    (a) depositing a sacrificial layer on a substrate to form a first layer;
    (b) depositing a conductive second layer on the first layer to form a layered substrate;
    (c) patterning the layered substrate to fabricate a multitude of patterned two dimensional faces;
    (d) patterning a hinge on an interface between adjacent patterned two dimensional faces;
    (e) patterning a hinge on an edge of the patterned two dimensional faces, wherein the hinge between two adjacent faces has a width that is about twice a width of the hinge on an edge;
    (f) depositing a material that can be liquefied on each hinge patterned in step (d) and step (e);
    (g) dissolving the sacrificial layer to release the patterned two dimensional faces therefrom;
    (h) heating the released patterned two dimensional faces to liquefy the material that can be liquefied deposited on each hinge, thereby self-assembling the three-dimensional container containing a fillable center chamber, whereupon cooling, the self-assembled three-dimensional container forms a three-dimensional container comprising a multitude of two dimensional faces permanently held together by solid hinges.

2. A three-dimensional container comprising a multitude of two-dimensional faces that form a hollow polyhedral shape and containing a fillable center chamber fabricated according to the method of claim 1.

3. The container according to claim 2, wherein the two-dimensional faces are patterned with perforations or pores.

4. The container according to claim 3, wherein the perforations or pores were created photolithographically.

5. The container according to claim 3, wherein the perforations or pores have a size from about 0.1 nm to about 100 microns.

6. The method according to claim 1, wherein the material that can be liquefied is a solder, a metallic alloy, a polymer or a glass.

7. The method according to claim 1, further comprising patterning the layered substrate by photolithography.

8. The container according to claim 2, wherein the container has a size that is microscale or nanoscale.

9. The method according to claim 1, further comprising patterning the two-dimensional faces with perforations or pores.

10. The method according to claim 9, wherein the perforations or pores are created photolithographically.

11. The method according to claim 9, wherein the perforations or pores have a size from about 0.1 nm to about 100 microns.

12. The container according to claim 2, wherein the container is a Faraday cage.

* * * * *